United States Patent [19]
Olesen

[11] Patent Number: 4,487,155
[45] Date of Patent: Dec. 11, 1984

[54] PNEUMATICALLY POWERED OXYGEN PRESSURE LOSS ALARM SYSTEM

[75] Inventor: Russell Olesen, Huntington, N.Y.

[73] Assignee: Puritan-Bennett Corporation, Kansas City, Mo.

[21] Appl. No.: 404,698

[22] Filed: Aug. 3, 1982

[51] Int. Cl.³ .............................................. G01L 19/12
[52] U.S. Cl. ...................................... 116/70; 137/557; 128/203.12
[58] Field of Search ...................... 116/70; 128/203.12, 128/203.14; 137/557

[56] References Cited

U.S. PATENT DOCUMENTS 3,870,012 3/1975 Metivier ................................ 116/70
4,176,617 12/1979 Pilipski .................................. 116/70
4,237,813 12/1980 Howison ............................... 116/70

Primary Examiner—Charles Frankfort
Assistant Examiner—Denis E. Corr
Attorney, Agent, or Firm—Fulwider, Patton, Rieber, Lee & Utecht

[57] ABSTRACT

A pneumatically powered oxygen pressure loss alarm system for use in conjunction with a gas anesthesia machine having an oxygen supply circuit and a gas mixing circuit. The oxygen pressure loss alarm system comprises a volume chamber in which a pressurized volume of oxygen is maintained, an oxygen escape valve for venting the chamber when pressure within the oxygen supply circuit falls below a critical minimum level, and an audible alarm operable in response to the flow of oxygen vented from the chamber through the oxygen escape valve. In addition, a reverse flow of residual gas from the gas mixing circuit, through a master valve also used to shut off the gas anesthesia machine, is coupled to the alarm to provide an audible indication of machine shut-down.

4 Claims, 1 Drawing Figure

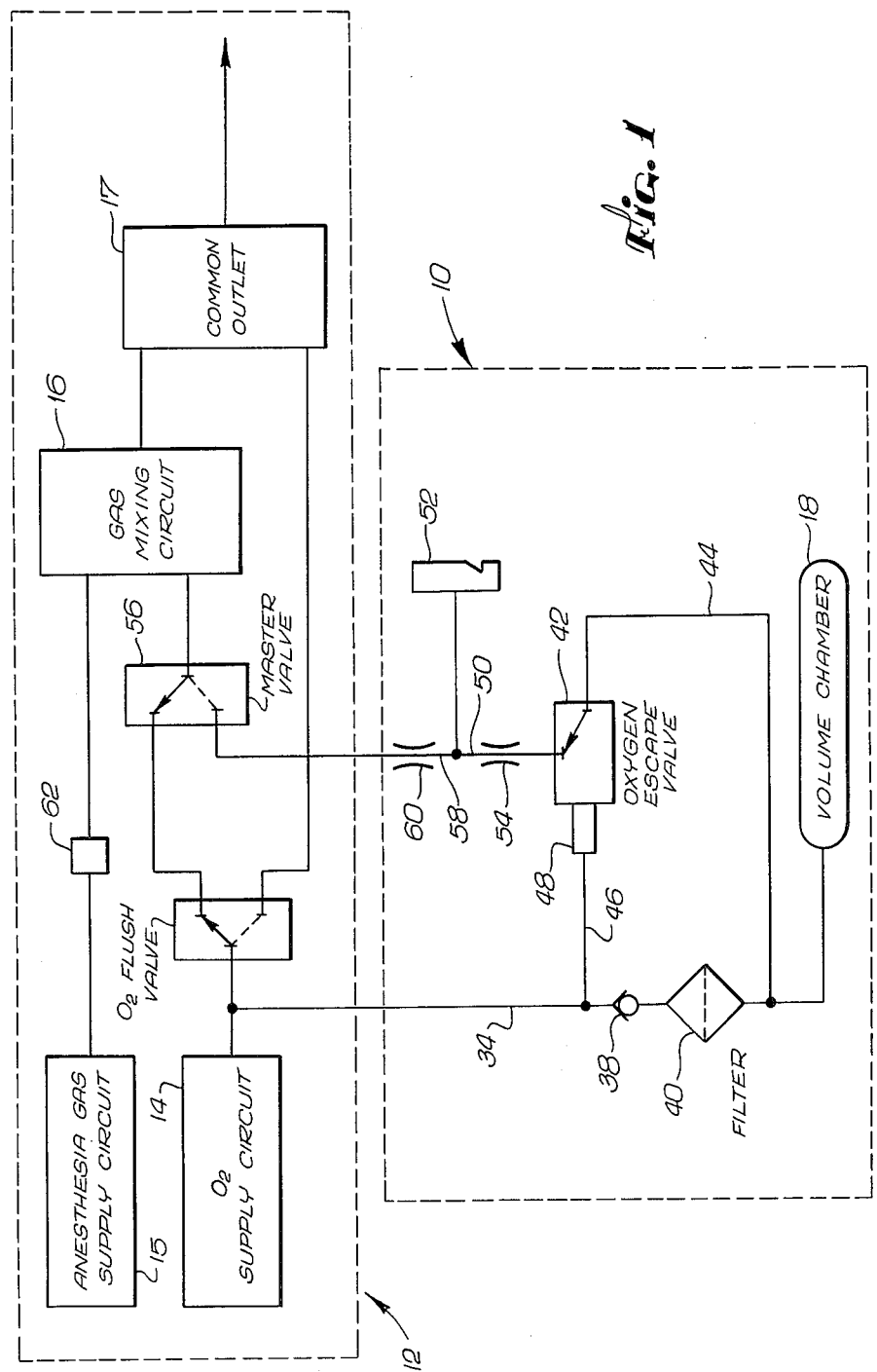

PNEUMATICALLY POWERED OXYGEN PRESSURE LOSS ALARM SYSTEM

BACKGROUND OF THE INVENTION

The present invention relates generally to gas anesthesia machines, and more particularly, to alarm systems for use in conjunction with gas anesthesia machines, to detect a loss of oxygen pressure.

A gas anesthesia machine typically comprises an oxygen supply circuit and an anesthesia gas supply circuit, for anesthesia gas such as nitrous oxide ($N_2O$), a gas mixing circuit wherein oxygen and anesthesia gas are mixed together and a common outlet through which a mixture of the gases is passed to a patient breathing circuit. The patient breathing circuit, which forms no part of the present invention, is ordinarily a closed-circuit system including a carbon dioxide absorber and at least two check valves, to ensure that a patient inhales gas from the common outlet and exhales through the carbon dioxide absorber. The patient breathing circuit may also employ a ventilator to pump breathing gas into the patient's lungs and a gas evacuation system for removal of excess gas.

The oxygen supply circuit of the anesthesia machine is pressurized to ensure the delivery of a proper flow of oxygen to a patient. The maintenance of the oxygen flow above a critical minimum level is important to protect the patient from injury from oxygen deprivation.

Occasionally, pressure within the oxygen supply circuit may fall below the critical level. For example, a malfunction in the oxygen supply circuit, such as a leak, may lead to a pressure drop within the circuit and a corresponding decrease in oxygen flow to the patient. As a result, the patient is in danger of serious injury unless an operator of the gas anesthesia machine quickly restores a safe oxygen flow. Although other oxygen pressure loss alarms have been used in the past, none has been completely satisfactory in all respects. Ideally, an oxygen pressure loss alarm should be pneumatically operated, for reliability, and should be responsive not only to loss of pressure due to duration of the oxygen supply, but also to pressure loss that occurs upon shutting off the gas anesthesia machine. The present invention is directed to these ends.

SUMMARY OF THE INVENTION

The present invention resides in a pneumatically powered oxygen pressure loss alarm system, for use in conjunction with a gas anesthesia machine having a pressurized oxygen supply circuit, to provide an alarm when oxygen pressure within the oxygen supply circuit decreases below a predetermined minimum level.

In broad terms, the oxygen pressure loss alarm system comprises a chamber for holding a pressurized volume of oxygen. A first oxygen line connects the chamber to a pressurized source of oxygen, and a one-way check valve prevents oxygen backflow out of the chamber through the first oxygen line. Oxygen escape valve means connected to the chamber is switchable from a closed to an open position to permit oxygen to escape from the chamber in response to a drop in oxygen pressure below a predetermined level. A second oxygen line connects the oxygen escape valve means to the oxygen supply circuit so that the oxygen escape valve means can monitor pressure within the supply circuit. A third oxygen line connects the oxygen escape valve means to alarm means responsive to a flow of gas. Oxygen escaping from the chamber when the oxygen escape valve means is in an open position flows through the third oxygen line and actuates the alarm means.

In a presently preferred embodiment of the invention, the chamber is connected to a pressurized oxygen source, such as the oxygen supply circuit, such that oxygen can flow to the chamber from the pressurized oxygen source through the first oxygen line, which is provided with a one-way check valve to prevent oxygen from flowing back out of the chamber. Thus, once the chamber has been charged with a volume of oxygen, it can hold the oxygen in a pressurized state.

A pressure-actuated pilot valve switchable between open and closed positions is also connected to the chamber. When the pilot valve is in a closed position, the pressurized oxygen remains trapped within the chamber, and when it is in an open position, oxygen can escape from the chamber.

A valve actuator cooperates with the pilot valve to cause it to open and close in response to variations in the oxygen supply pressure. The second oxygen line connects the valve actuator to the oxygen supply circuit. When pressure within the supply circuit exceeds a predetermined minimum level, the valve actuator causes the pilot valve to close, preventing oxygen from escaping from the chamber. When pressure within the oxygen supply circuit falls below the predetermined minimum level, the valve actuator causes the pilot valve to open, and oxygen to escapes from the chamber.

The third oxygen line connects the pilot valve to the alarm means. Thus, when pressure within the oxygen supply circuit falls below the critical minimum level, and the valve actuator causes the oxygen escape valve means to open, the escaping oxygen flows through the third oxygen line to the alarm means, which responds by providing an alarm to alert an operator of the anesthesia machine. The operator can then take appropriate steps to restore a proper oxygen pressure within the oxygen supply circuit or to otherwise protect the patient from serious injuries. The alarm means in the presently preferred embodiment of the invention is a whistle, which provides an audible alarm in response to the flow of oxygen from the chamber.

In addition, the presently preferred embodiment includes a filter located in the first oxygen line to remove impurities, such as dust, and a first flow restrictor with its inlet side attached to the pilot valve located in the third oxygen line. The first flow restrictor can be selectively adjusted to vary the flow of oxygen through the third line to control the pitch of the sound produced by the alarm means.

Another feature of the present invention is the use of the alarm means in conjunction with a master valve connected to the anesthesia machine. When the master valve is in a first position, oxygen from the oxygen supply circuit can flow into the gas mixing circuit wherein it can be mixed with anesthesia gas prior to being delivered to the patient. When the master valve is in a second position, oxygen flow into the gas mixing circuit is stopped, and gas can flow back out of the gas mixing circuit, through the master valve and to the alarm means, which produces an alarm in response to this gas flow.

Typically, the master valve is manually switched from the first to the second position when the gas anesthesia machine is turned off. The alarm produced by the gas flowing from the gas mixing circuit is generally of short duration; it lasts until the gas has been exhausted from the gas mixing circuit. The alarm when used in this manner indicates to the operator that the machine is no longer providing oxygen to the patient.

An optional second flow restrictor can be provided with its inlet end connected to the master valve to permit the adjustment of the flow of gas from the gas mixing circuit, to control the pitch and duration of the alarm produced by the alarm means.

Other advantages and features of the present invention will become apparent from the following more detailed description, taken in conjunction with the accompanying drawings which illustrates, by way of example, the principles of the invention.

BRIEF DESCRIPTION OF THE DRAWING

FIG. 1 is a schematic view of a pneumatically powered oxygen pressure loss alarm system connected to a gas anesthesia machine in accordance with the invention.

DESCRIPTION OF THE PREFERRED EMBODIMENT

As shown in the exemplary drawings, the present invention is embodied in a novel pneumatically operated oxygen pressure loss alarm system designated generally by reference numeral 10, for use in conjunction with a gas anesthesia machine 12 having an oxygen supply circuit 14, an anesthesia gas supply circuit 15 and a gas mixing circuit 16, in which the oxygen and anesthesia gas are mixed prior to being passed to a common outlet 17, for connection to a patient breathing circuit (not shown). In accordance with the invention, the oxygen pressure loss alarm system 10 provides an alarm in response to a drop in oxygen pressure, within the oxygen supply circuit 14, below a critical minimum level. In addition, the alarm system may be responsive to a reverse flow of gas from the gas mixing circuit 16. A loss of pressure within the oxygen supply circuit 14 or a gas outflow from the gas mixing circuit 16 can result in a reduced oxygen flow to a patient which can, in turn, cause severe injury due to oxygen deprivation. An audible alarm produced by the oxygen pressure loss alarm system 10 alerts an operator of the gas anesthesia machine 12 to such a loss of oxygen pressure or outflow of gas so that he can act promptly to restore a safe oxygen flow to the patient.

As shown in the drawings, the oxygen pressure loss alarm system 10 includes a chamber 18 connected to the oxygen supply circuit 14 by a first oxygen line 20. Pressurized oxygen from the oxygen supply circuit 14 can flow from the oxygen supply circuit 14 through the first oxygen line 20 and into the chamber 18 which becomes charged with a pressurized volume of oxygen.

A one-way check valve 22, such as a valve manufactured as part number JCV-1 by the Clippard Company of Cincinnati, Ohio, is connected in the first oxygen line 20 to prevent oxygen backflow from the chamber 18 through the first oxygen line. Thus, when the chamber 18 is pressurized to the supply pressure, oxygen cannot escape through the first oxygen line 20. A filter 24, of conventional design, for removing solid impurities from the oxygen flow, is also located in the first oxygen line 20.

A pilot valve 28, such as a two-way spool valve manufactured as part number MJVO-2 by the Clippard Company, is also connected to the chamber 18. When the pilot valve 28 is closed, oxygen contained within the chamber 18 remains trapped therein, and when the pilot valve is open, oxygen can escape through the valve.

A second oxygen line 30 connects a valve actuator 32, such as a miniature pilot actuator, manufactured as part number MPA-3P by the Clippard Company, to the first oxygen line 20 which is in fluid communication with the oxygen supply circuit 14. The valve actuator 32 operates in response to a drop below a critical minimum level in oxygen pressure within the oxygen supply circuit 14. The valve actuator 32 cooperates with the pilot valve 28 and causes it to open when oxygen pressure within the oxygen supply circuit 14 drops below a critical minimum level, and causes it to close when oxygen pressure in the supply circuit 14 exceeds that level. Thus, oxygen can flow out of the chamber 18 when oxygen pressure within the oxygen supply circuit 14 is below the critical minimum level, and oxygen remains trapped within the volume chamber when oxygen pressure within the oxygen supply circuit 14 exceeds the critical level.

A third oxygen line 34 connects the pilot valve 28 to a whistle 36. Oxygen escaping from the chamber 18 flows through the third oxygen line 34 to the whistle 36 which produces a distinctive audible alarm in response to the flow. The whistle alerts the operator to a dangerous loss of pressure within the oxygen supply circuit 14, and the operator can then take steps to restore proper oxygen pressure or to provide an alternate supply of oxygen for the patient.

An optional first flow restrictor 40 having its inlet end connected to the pilot valve 28, can be provided to adjust the flow of oxygen through the third oxygen line 34. Adjustment of the oxygen flow enables the operator to vary the frequency of the alarm produced by the whistle 36.

An additional feature of the present invention is the manner in which the alarm system 10 cooperates with a master valve 42 used to switch off the entire anesthesia machine 12. When a mixture of oxygen and anesthesia gas is being provided to the patient by the gas anesthesia machine 12, the master valve 42 is in an ON position, and oxygen from the oxygen supply circuit 14 flows through the master valve into the gas mixing circuit 16, where it is mixed with anesthesia gas and delivered to the patient. When the gas anesthesia machine is turned off, the master valve 42 is switched to an OFF position, and the oxygen supply circuit 14 is disconnected from the gas mixing circuit 16, and the gas mixing circuit is connected to a gas line 44 connected to the whistle 36. At the same time, the loss of oxygen pressure downstream of the master valve 42 results in closing of a pressure actuated stop valve 46 in the anesthesia gas supply circuit 15, thereby shutting off the anesthesia gas. An outflow of gas from the gas mixing circuit 16 through the gas line 44 activates the whistle 36 and produces an audible alarm, which lasts until all the remaining gas is vented from the gas mixing circuit 16.

An optional second flow restrictor 50 having its inlet end connected to the master valve 42 can be used to adjust the flow of the gas mixture through the gas line 44. Adjustment of the gas flow permits the operator to adjust the audible frequency of the alarm produced by the whistle 36 when gas flows from the gas mixing circuit 16.

The gas anesthesia machine 12 is provided with a two position oxygen flush valve 52, which forms no part of the present invention. The flush valve can be selectively switched to connect the oxygen supply circuit 14 either to the master valve 42 and gas mixing circuit 16, or directly to the common outlet 17.

From the foregoing, it will be appreciated that the present invention provides a novel oxygen pressure loss alarm system for use in conjunction with a gas anesthesia machine, to produce an alarm in response to a drop in oxygen pressure below a critical minimum level. In addition, the presently preferred embodiment of the invention can also produce an alarm in response to a reverse outflow of gas when the gas anesthesia machine is switched off. The invention therefore provides a pneumatically powered system which can warn the operator of the gas anesthesia machine when there are potentially dangerous losses of oxygen from the oxygen supply circuit, or when the gas anesthesia machine has been turned off, so that he can then take appropriate steps to avert harm to a patient.

While a particular form of the invention has been illustrated and described in detail, it will be appreciated that various modifications and improvements can be made without departing from the spirit and scope of the invention. Accordingly, it is not intended that the invention be limited except by the appended claims.

I claim:

1. A pneumatically operated oxygen pressure loss alarm system for use in conjunction with a gas anesthesia machine having an oxygen supply circuit, said system comprising:
    a chamber in which a pressurized volume of oxygen can be maintained;
    a first oxygen line for connecting said chamber to a pressurized oxygen source;
    one-way check valve means for preventing a backflow of oxygen from said chamber through said first oxygen line;
    oxygen escape valve means connected to said chamber and switchable from a closed to an open position in response to a drop in oxygen supply circuit pressure below a predetermined level;
    a second oxygen line for connecting said oxygen escape valve means to the oxygen supply circuit to permit said oxygen escape valve means to monitor oxygen pressure within the oxygen supply circuit;
    alarm means responsive to a flow of gas;
    a third oxygen line for connecting said oxygen escape valve means to said alarm means such that oxygen can flow from said chamber through said third oxygen line, to actuate said alarm means when said oxygen escape valve means is in an open position; and
    master valve means operable to disconnect the gas anesthesia machine from its oxygen supply circuit, and to simultaneously connect the alarm means in fluid communication with residual gases in the gas anesthesia machine, whereby the residual gases are vented through said alarm means to provide an indication that the anesthesia machine has been shut off.

2. A pneumatically operated oxygen pressure loss alarm system as set forth in claim 1, and further comprising:
    second flow restrictor means to provide adjustment of the flow rate of residual gases from said master valve means through said alarm means.

3. A pneumatically operated oxygen pressure loss alarm system for use in conjunction with a gas anesthesia machine having an oxygen supply circuit, said system comprising:
    a chamber in which a pressurized volume of oxygen can be maintained;
    a first oxygen line connecting said chamber to a pressurized oxygen source;
    one-way check valve means for preventing a backflow of oxygen from said chamber through said first oxygen line;
    pilot valve means connected to said chamber and switchable between a closed and an open position;
    valve actuator means connected to said pilot valve means for selectively opening and closing said pilot valve means in response to pressure changes within the oxygen supply circuit;
    a second oxygen line for connecting said valve actuator means to the oxygen supply circuit to permit said actuator valve means to monitor oxygen pressure within the oxygen supply circuit;
    alarm means responsive to a flow of gas;
    a third oxygen line for connecting said pilot valve means to said alarm means such that oxygen can flow from said chamber through said third oxygen line to actuate said alarm means when said pilot valve means is in an open position;
    an additional gas line connected to said alarm means; and
    master valve means for disconnecting the gas anesthesia machine from its oxygen supply circuit, and simultaneously connecting a gas mixing circuit of the gas anesthesia machine to said additional gas line leading to said alarm means, such that when the gas mixing circuit is connected to said additional gas line, gas from the gas mixing circuit can flow through said gas line, to actuate said alarm means.

4. A pneumatically operated oxygen pressure loss alarm system as set forth in claim 3, and further comprising:
    second flow restrictor means in said additional gas line, to permit adjustment of the flow rate of gas through said additional gas line to said alarm means.

* * * * *